(12) United States Patent
Holm-Kennedy

(10) Patent No.: US 8,536,661 B1
(45) Date of Patent: Sep. 17, 2013

(54) BIOSENSOR CHIP SENSOR PROTECTION METHODS

(75) Inventor: James W. Holm-Kennedy, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 1036 days.

(21) Appl. No.: 11/167,913

(22) Filed: Jun. 27, 2005

Related U.S. Application Data

(60) Provisional application No. 60/582,928, filed on Jun. 25, 2004, provisional application No. 60/582,952, filed on Jun. 25, 2004, provisional application No. 60/582,959, filed on Jun. 25, 2004, provisional application No. 60/582,760, filed on Jun. 25, 2004.

(51) Int. Cl.
*H01L 27/14* (2006.01)

(52) U.S. Cl.
USPC .................................. 257/414; 257/E27.001

(58) Field of Classification Search
USPC .............................. 257/414, 253; 438/48, 49
See application file for complete search history.

(56) References Cited

U.S. PATENT DOCUMENTS

| | | | |
|---|---|---|---|
| 4,238,757 A * | 12/1980 | Schenck | 257/253 |
| 4,773,970 A * | 9/1988 | Purbrick et al. | 205/778.5 |
| 4,885,623 A | 12/1989 | Holm-Kennedy et al. | |
| 4,916,505 A | 4/1990 | Holm-Kennedy | |
| 4,926,682 A | 5/1990 | Holm-Kennedy et al. | |
| 4,926,693 A | 5/1990 | Holm-Kennedy et al. | |
| 4,951,510 A | 8/1990 | Holm-Kennedy et al. | |
| 4,960,177 A | 10/1990 | Holm-Kennedy et al. | |
| 5,036,286 A | 7/1991 | Holm-Kennedy et al. | |
| 5,083,466 A | 1/1992 | Holm-Kennedy et al. | |
| 5,095,762 A | 3/1992 | Holm-Kennedy et al. | |
| 5,101,669 A | 4/1992 | Holm-Kennedy et al. | |
| 5,140,393 A | 8/1992 | Hijikihigawa et al. | |
| 5,466,348 A | 11/1995 | Holm-Kennedy | |
| 5,770,076 A * | 6/1998 | Chu et al. | 210/490 |
| 5,784,507 A | 7/1998 | Holm-Kennedy et al. | |
| 2002/0006632 A1 * | 1/2002 | Ponnampalam et al. | 435/7.92 |
| 2003/0029245 A1 * | 2/2003 | Izadnegahdar et al. | 73/753 |
| 2003/0178641 A1 * | 9/2003 | Blair et al. | 257/200 |

FOREIGN PATENT DOCUMENTS

| | | |
|---|---|---|
| JP | 55-010546 A | 1/1980 |
| JP | 08-313476 A | 11/1996 |
| WO | WO 01/64945 A2 | 9/2001 |

* cited by examiner

*Primary Examiner* — Ha Tran T Nguyen
*Assistant Examiner* — Kevin Quinto
(74) *Attorney, Agent, or Firm* — James Creighton Wray

(57) ABSTRACT

Receptors are selectively attached by introducing blocking materials in the areas outside the active sensor surface area, and/or selectively attaching the bio receptors to one or more active sensor surface areas. Methods for selective attachment include the use of optical attachment using a patterned exposure to assist in the creation of receptor bonding to preselected regions of the one or more chips. Blocking agents are attached to regions where blocking the receptor attachment is beneficial. Biased conducting regions may also affect selective attachment. Such controlled blocking may be accomplished using optical patterning exposure with optical assisted bonding of the blocking molecule or lift off processes. Patterned exposure for either attachment assists or liftoff processes employs photo masks. Conducting regions outside of the active sensor gate region are biased, affecting biochemical binding or non binding, and shielding of the semiconductor region outside of the active biosensor region.

28 Claims, 4 Drawing Sheets

BIOSENSOR CHIP SENSOR PROTECTION METHODS

This application claims the benefit of U.S. Provisional Application No. 60/582,928, filed Jun. 25, 2004, U.S. Provisional Application No. 60/582,952, filed Jun. 25, 2004; U.S. Provisional Application No. 60/582,959, filed Jun. 25, 2004, and U.S. Provisional Application No. 60/582,760, filed Jun. 25, 2004, which are hereby incorporated by reference in their entirety.

BACKGROUND OF THE INVENTION

Biosensors have been and are being developed to detect, identify and quantify various biochemicals, ranging from proteins to toxins to RNA to c-DNA to oligos and to disease agents such as viruses, bacteria, spores and Prions. This list is by way of example, and is not intended to be complete. Some biosensors sense charge on the molecule. Many biochemicals carry a net charge. Electrophoresis methods and various blots exploit molecule net charge to affect physical separation of such molecules.

The cost of biosensor manufacturing is impacted by chip design, integrated circuits, packaging, chemical processing and biochemical receptor costs.

Needs exist for reducing the cost and the number of biochemical receptors used for detection, and improving the use of biochemical receptors for maintaining minimum costs while ensuring maximum sensor performance.

SUMMARY OF THE INVENTION

The present invention is a biosensor apparatus that includes a substrate, a sensor positioned in or on the substrate, an insulator over the sensor, a gate region positioned on the insulator, receptors held on the gate region for attaching targeted biochemical materials, and a chemical attachment blocking layer overlying the protective insulation layer for blocking attachment of receptors and/or attachment of targeted biochemical materials to the biosensor apparatus other than on the gate region.

The present invention may also include a gate region chemical attachment layer positioned on the gate region. A photo mask may cover the chemical attachment blocking layer, and the gate region is exposed to light for bonding pre-selected chemicals to the gate region. Alternatively, a photo mask covers the chemical attachment blocking layer, and the receptors on the gate region are exposed to light for bonding pre-selected chemicals to the receptors on the gate region.

A chemical attachment blocking layer may be located on the protective insulating region. A photo mask may cover the apparatus and masking the gate region for exposing the chemical attachment blocking layer to light.

The chemical attachment blocking layer may be a biochemical layer, an inert coating, and/or conductive shielding.

In another embodiment, a sensor apparatus includes a semiconductor substrate, a sensor layer in or on the substrate, an active gate attachment region on the sensor layer, a first insulator layer covering the substrate layer apart from the sensor layer, a conductor layer covering the first insulator layer, and a second insulator layer covering the conductor layer.

A circuit is connected to the sensor layer and to the semiconductor substrate, a substrate back gate bias potential connected to the circuit. The circuit is a first circuit that also includes a second circuit connected to the conductor layer and to the first circuit. A surface protection bias voltage is connected to the second circuit. The circuit is connected to the conductor layer and to the sensor layer. A surface protection bias voltage is connected to the circuit.

A chemical attachment blocking layer is located on the protective insulating region. Alternatively, the first or second protective insulating layer is a biochemical layer, an inert coating, or conductive shielding. The sensor apparatus is resistant to degradation from biochemical influences.

These and further and other objects and features of the invention are apparent in the disclosure, which includes the above and ongoing written specification, with the drawings.

DETAILED DESCRIPTION OF THE PREFERRED EMBODIMENTS

Figure 1:
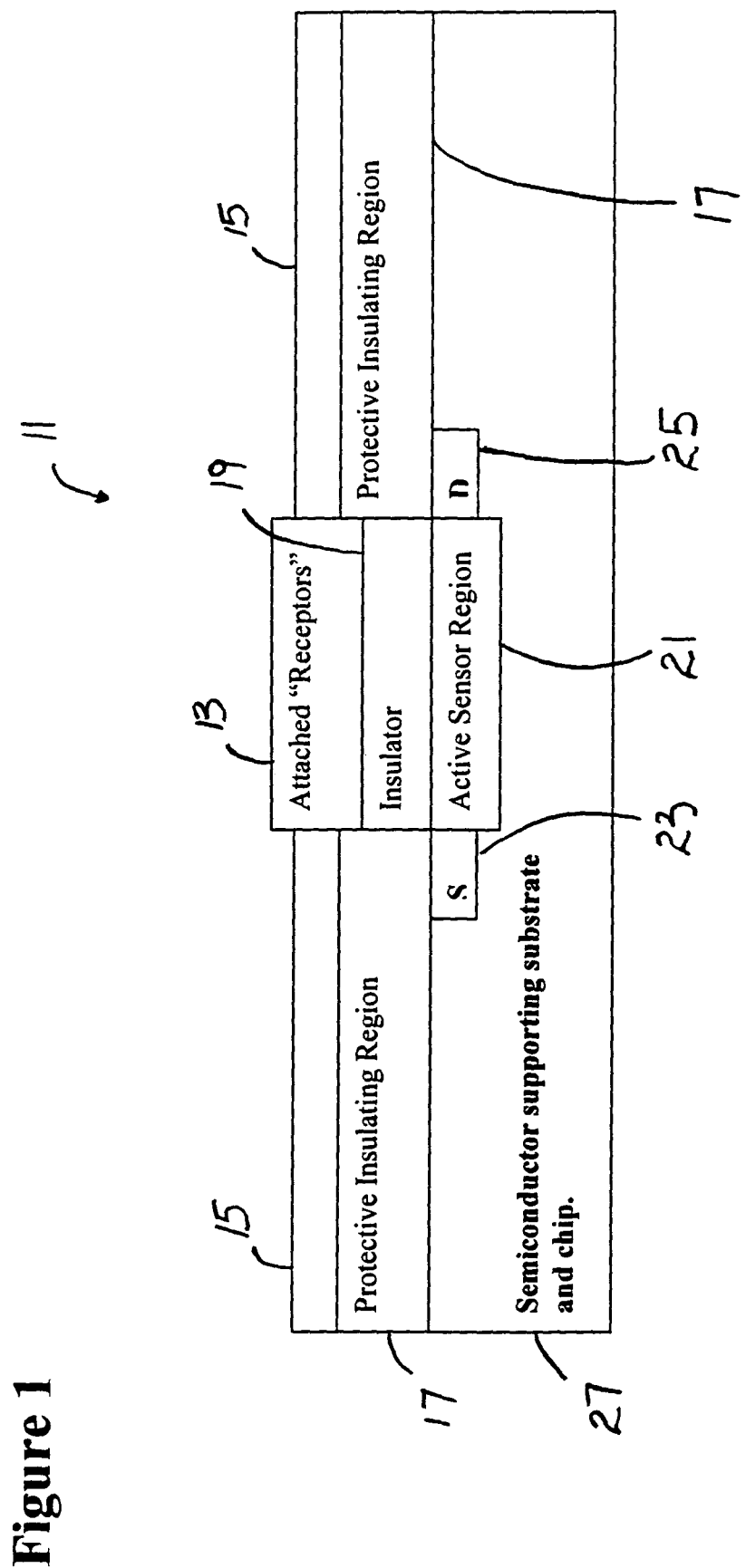
FIG. 1 is a sensor chip patterned with active and non-active regions.

Biochemicals are attached to the active surface area of semiconductor-based biosensors. Such receptors may be expensive. The receptors must be bound to the surface of the biochemical sensor but in general my also bind to other surface areas. The active sensor surface area may be a very small portion of the total chip surface, circuit surface and/or packaging surface, e.g. <<1%. A portion of the cost of the manufacture of biosensors and biosensor arrays is the cost of the receptors, such as antibodies and oligos. Such receptor costs may be very high. For example, this may be the case for rare antibodies or oligos fabricated in very small quantities, or portions of DNA or RNA refined from various sources. A method of attaching the receptors specifically and exclusively to the active area where they are needed creates a significantly reduced product cost. This also eliminates certain potential sources of error and interference with the sensor detection output signal.

In the present invention receptors are selectively attached by introducing blocking materials in the areas outside the active sensor surface area, and/or selectively attaching the bio receptors to one or more solely active sensor surface areas. Methods for this selective attachment include the use of optical attachment using a patterned exposure to assist in the creation of receptor bonding to pre-selected regions of the one or more chips. Blocking agents attached to regions where blocking the receptor attachment is beneficial may also be used. Such controlled blocking may be accomplished using optical patterning exposure with optical assisted bonding of the blocking molecule or lift off processes as used in the semiconductor industry. Patterned exposure for either attachment assists or liftoff processes may employ photo masks as commonly used in the semiconductor industry.

Electrical assists to attract the receptor molecules to a pre-selected active sensor region may be used. Similar processes may be used to attract blocking compounds to preselected blocking regions.

These methods may be used on individual sensors, chips with sensor arrays, or on entire wafers in a batch processing approach to reduce manufacturing costs.

Biochemicals in general and proteins in particular can be sticky, attaching themselves to all or many available surfaces with functional groups or binding sites. Such chemicals may be expensive. Additionally, attachment of chemicals to the chip surface outside of the active sensor region can create problems in the sensor operation and accuracy.

Such patterning of blocking agents may include the use of preselected hydrophilic and hydrophobic regions.

In the present invention the charges associated with the biochemicals attached outside of the gate region may introduce influences on the underlying chip and integrated circuitry, for example. It is desirable to keep the attachment of receptor molecules confined to the biosensor active (gate) region. It is further desirable to block the attachment of biochemicals and other chemicals to the regions outside of the active sensor region. This blocking is important where the chemicals blocked, and which would have attached, provide an undesirable influence on the underlying chip regions via chemical potential or electric field arising from biochemically or target incorporated surface charge.

The present invention provides selective attachment of specific chemicals to pre-selected regions of the chip. Both selective attachment of receptor molecules and selective attachment of blocking materials, agents or molecules are provided. Receptors are defined in terms of chemical reactions and specificity. Here receptor refers to a generic class of molecules that provide chemical reaction with a target molecule and react specifically with said target molecule. This definition is intended to be very general, and not limiting to cell and similar receptors. Blocking in this context refers to the use of any substance or coating that prevents pre-selected chemicals, which, for example, may be all biochemicals, from attaching.

Some attachment methods are presented by way of example. There are many ways to attached pre-selected chemicals to pre-selected regions.

Photo assisted bonding may be employed. Photo assisted bonding of biochemicals to a pre-selected region of the chip may be used. Photochemical attachment and reaction assisted chemistry are used in preparation of gene chips.

Figure 2A:
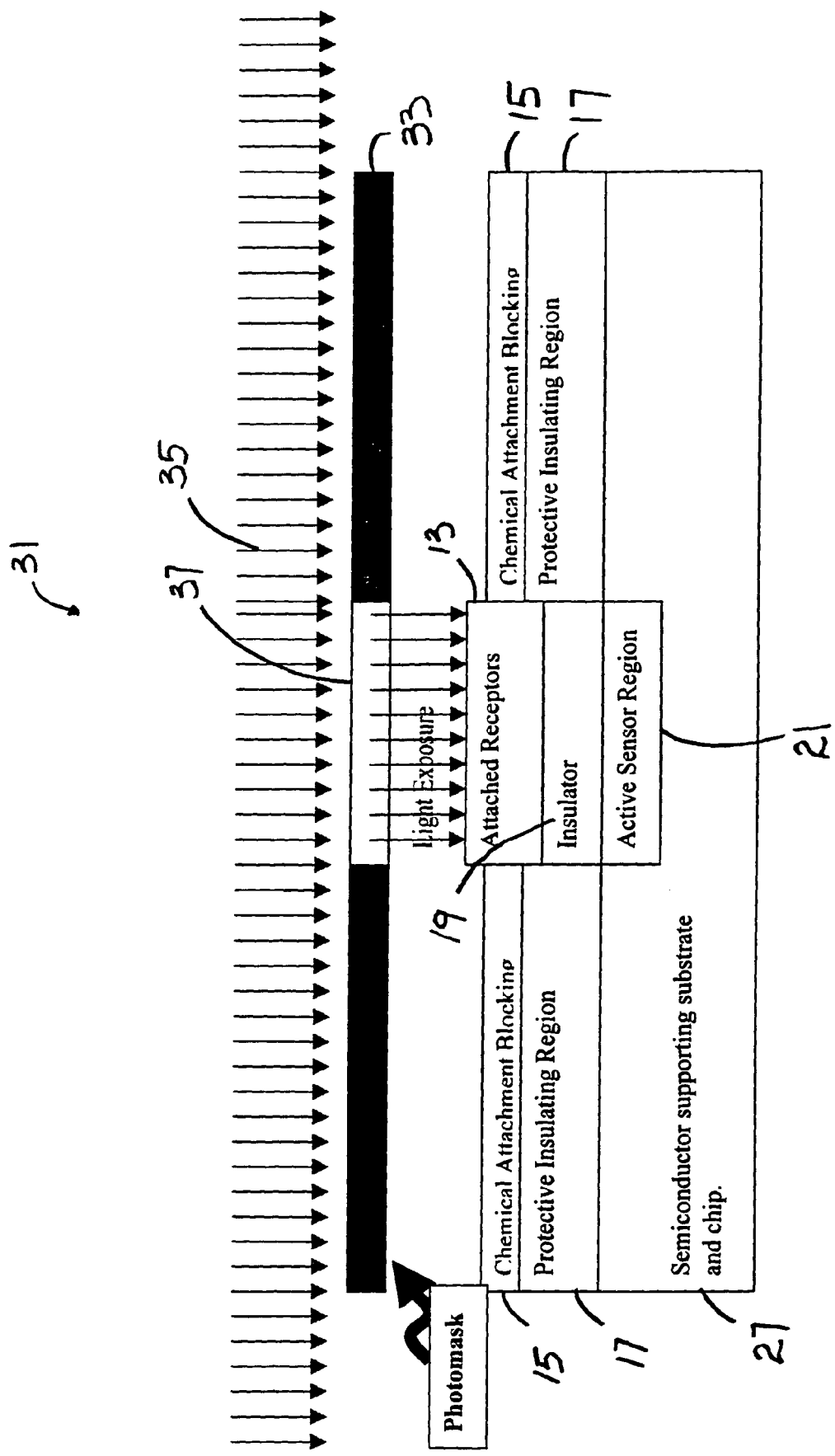
FIG. 2A is a photolithographic assisted gate chemical attachment.
Figure 2B:
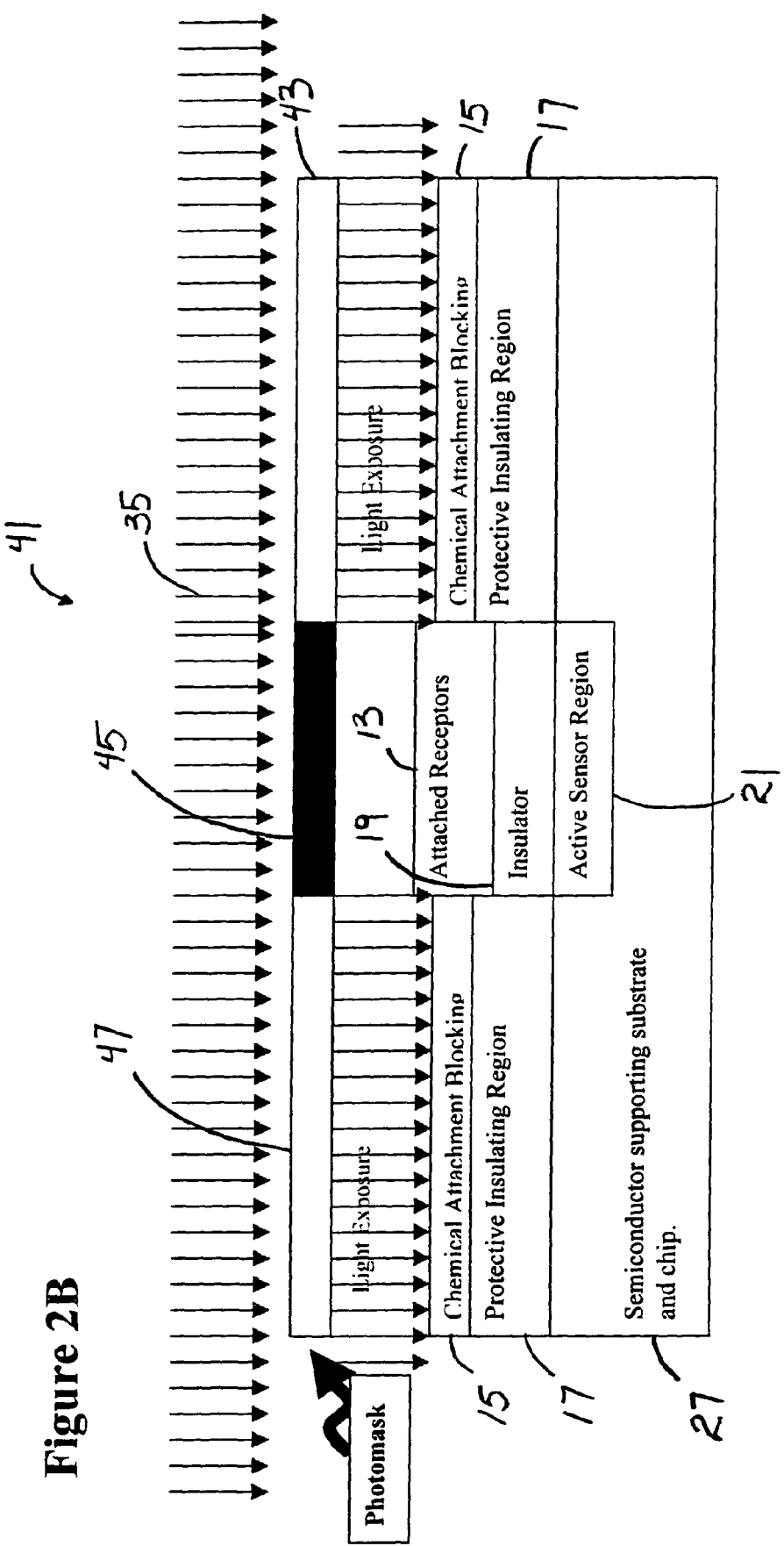
FIG. 2B is a photo-assisted attachment of chemical reaction blocking materials.

FIG. 2B shows photo-assisted attachment of chemical reaction blocking materials 41. A photo mask 43 is shown with pre-selected regions made opaque 45 over an active sensor region 21, i.e., the gate region. Pre-selected transparent portions 47 are shown over the regions where a pre-selected material is attached to block the receptor and target attachment. By selecting the correct blocking material or materials, both the target's receptors and the target and other chemicals are prevented from attaching to regions of the chip outside of the biochemical active sensor region. An attached receptor region 13 is patterned so the receptor region only consumes receptors during manufacture. A remaining region 15 is coated with material that blocks chemical attachment. A protective insulating region 17 underlies the chemical attachment blocking regions 15. An insulator 19 is located between the attached receptors 13 and an active sensor region 21. A source 23 is connected to the active sensor region 21 remote from a drain 25. The active sensor region 21 is located in or on a semiconductor supporting substrate and chip 27.

Electrical assisted bonding may be used. The chip may be patterned with selective conductive structures, such as are used in integrated circuit interconnects, to provide either attractive and/or repulsive electric fields. By way of example, a voltage may be applied to the Source S and Drain D, as shown in FIG. 1, to create an electric field above the active sensor gate region that repels and/or attracts pre-selective charges. Similar fields penetrating the environment outside of the chip insulator regions may be generated using pre-selected and selectively patterned conductors. Such conductors can selective attract and/or repel charged molecules depending on the voltage selected and charges on the molecules. It may be advantageous to place an electrode (not shown) in solution above the active gate region to support such attachment and repulsion.

FIG. 1 is a sensor chip 11 patterned with active and non-active regions. The attached receptor region 13 is patterned so the active gate receptor region only consumes receptors during manufacture. The remaining region 15 is coated with material which blocks chemical attachment. A protective insulating region 17 underlies the chemical attachment blocking regions 15. An insulator 19 is located between the attached receptors 13 and an active sensor region 21. A source 23 is connected to the active sensor region 21 remote from a drain 25. The active sensor region 21 is located in or on a semiconductor supporting substrate and chip 27.

Lift off processes may be employed. By selectively patterning a chip with a coating, such as is used routinely with photo resist, the region with the coating may be post processed to lift off and take whatever has attached to that patterned region with the lift off coating. Washing or other mechanical, chemical or physical process may dispose of the lift off coating and subsequent unwanted layers that might alter the chip behavior in undesirable electronic ways.

Patterned blocking processes may be used. Materials may be patterned using photolithographic means, by way of example, to provide a pattern of material in a pre-selected region. This patterned material may be selected to block processes that are undesirable in that region, or to accept processes in a desired region. Such blocked processes and materials may include, by way of example, chemical attachment, including biochemicals, chemicals that may react with the underlying coatings and/or chemicals, pH sensitive materials, and charged materials and/or chemicals.

FIG. 2A shows photolithographic assisted gate chemical attachment 31. A partially opaque mask 33 with openings 37 only allows light 35 to fall on the active sensor region (gate) 21 where pre-selected biochemicals are chemically bonded using light assisted bonding. Covalent bonding is one preferred type of bonding to be affected using this process. For example, the strepaviden attachment process may be used.

Figure 3:
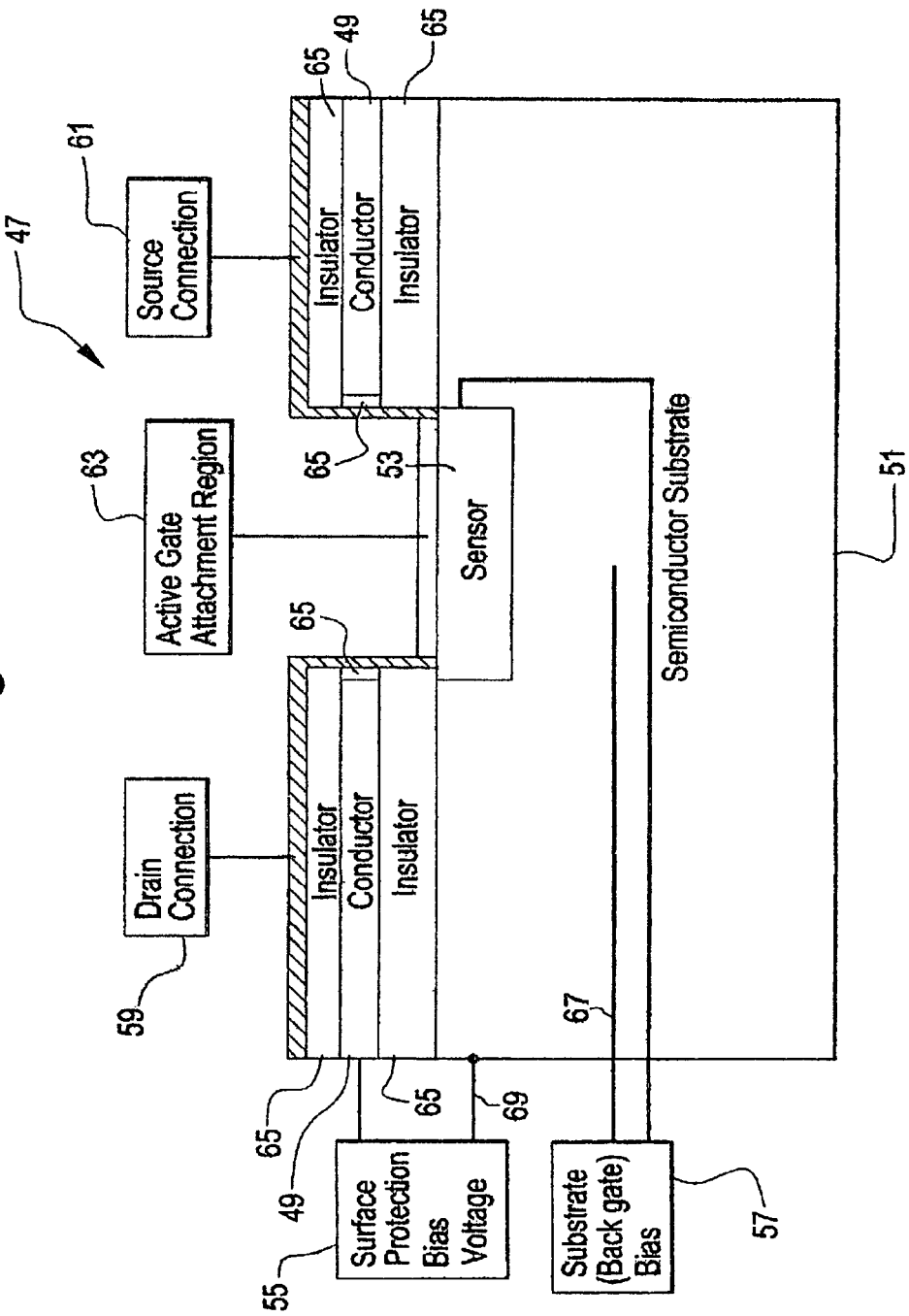
FIG. 3 shows a conductive protection layer.

FIG. 3 shows a conductive protection layer 47. A conductive region 49 is layered above a semiconductor 51 outside of a sensor area 53. This region is biased with the same voltage 55. Back gate bias 57 is connected to a first circuit 67, which is connected to the sensor region 53 and to the semiconductor substrate 51. Surface protection bias is connected to a second circuit 69 that connects to the conductive region 49 and first circuit 67. In this manner the surface is not inverted outside the sensor region and undesirable leakage current from a bulk inverted region does not occur. The conductive layer 49 may be used with device having other forms of isolation, such as trench isolation, or may provide protection from unwanted leakage and current measurement error introduction without the use of other sensor isolation. A drain connection 59 and a source connection 61 are connected to the sensor's 53 conducting channel. An active gate attachment region 63 is attached to the sensor. Insulator regions 65 surround the conductive regions 49. The source, drain, and any other electrical interconnects to the sensor and incorporated circuitry (if present) are of course necessarily covered with a protective coating, such as Silicon Nitride.

Several blocking methods may be used. Selective regions may be blocked from undesirable chemical attachment by placing in those regions chemicals that reject the unwanted attachment.

Non-reactive or inert materials may be applied in non-sensing regions. Non-reactive substances would, in this case, coat those regions where attachment is to be blocked. FIG. 1 illustrates attachment blocked regions. By way of example, Parylene, after curing to ensure chemical inactivity, may be used to coat those regions where chemical binding activity is to be suppressed. Other materials can be used to suppress or block chemical attachment. Non-reactive materials may be patterned using integrated circuit mask patterning methods and technologies.

Gate attachment coatings and/or fields may be applied in the sensing regions. The only region that needs the receptors is the active gate region or even just a portion of the active gate region. Limiting the attachment to just the active sensor region of the silicon chip provides a conservation of the active receptor species. In some cases such specific receptors may be costly. In such cases, such selective attachment of said receptors to only those regions where the reaction with the target molecule is to be sensed is appropriate and reduces waste, with attendant cost savings.

Such selective attachment to the gate region above the chip's active sensor region may be accomplished in various ways.

Using photolithographic methods and techniques, photo exposure can be used to assist bonding of the receptors (photochemistry). By way of example, attachment of strepaviden or oligos may be applied such as is used in gene chips to selective active regions, as shown in FIG. 1. Direct bonding of molecules to the active region using photo assisted bonding may be accomplished, or an intermediary chemical system such as the strepaviden biotin system may be used.

IV-B may be used to prepare surfaces or to fix coatings for preparing surfaces. The region outside the gate active region may be selectively coated, for example, with chemicals that reject the pre-selected receptor molecules that are to be located only in the gate active region. For example, a different but low cost receptor that is non-reactive with the target receptor may be used. Then, when the chip is re-exposed to the pre-selected receptor of interest, the only location it may bind is the active gate region.

Attachment prevention outside the sensor active regions may employ varied processes and chemicals. Blocking chemicals such as BSA are well known in the medical technology arts.

Blocking materials may be used. In addition to the use of non-binding materials coating the regions of the chip outside of the gate active region, materials that are non-attractive may be used. Selective chemical systems may be used. Some examples are described. Inert materials, as described above, may be used. Repulsive materials may be employed as blocking materials and include, by way of example, the following. Charged materials may be used. The charge may be of the same sign as the targeted binding receptor and thus provide repulsion of the receptor or target. Hydrophilic or hydrophobic materials may be used. The material is selected to pre-selectively repel the desired molecules or material attachment. Repelling biochemicals or other chemicals may be used. A previously attached coating of a chemical that will not react with the pre-selected receptor or target chemicals is attached in the region. For example, an antibody to Dengue virus would not be expected to bind to an antibody to some other virus or biochemical, in general. Such repelling chemicals would be selected with regard to non-reactivity and confirmed. By way of example, BSA is used for blocking purposes in medical technology to suppress non-specific binding to exposed binding sites. In the current application, however, entire regions would be coated with the blocking biochemical, which is not the case with conventional medical technology, in general.

By way of examples, such blocking chemicals that may be used include: other antibodies, oligos that do not react with the target, proteins that do not react with the target, polymers that do not react with the target, conductors that do not react with the target, selective DNA and/or RNA, and other nucleotide molecules, including individual nucleotides, target molecules themselves, and other materials and chemicals.

Sensor protection from conducting shorting effects on the chip uses pre-selected chemicals attached to the non-active sensor regions. Attachment of charges to regions outside the active sensor region may cause inversion or other charging effects of the surface between the semiconductor and the overlying insulator.

The region to be protected may be coated with: non-binding coatings, as described above, and/or chemicals with the same charge as the biochemicals to which the sensor is to be exposed.

The innovation applied to semiconductor sensors is not described in the prior art even though there is extensive literature over the years on semiconductor based sensors. The effect of biochemical attachment in causing inversion outside of the active sensor region and thus causing shorting effects of the underlying semiconductor region, including chip circuitry, is not found in the literature. Semiconductor base biosensors such as immunoFETs have been considered a largely failed technology due to drift and screening effects. The need for special configurations to address the issues described above has not been addressed.

Examples of chemical targets and applications regimes follow.

A partial list of biosensor applications target molecules is indicated in Table I. The list is by way of example. Applications targets are not limited to the list in Table I.

Applications of the Si based biosensor platform are described in general applications regimes, by way of example, by the list provided in Table II. Table II is intended to be a list of applications by way of example. Applications are not intended to be limited to this partial list.

While the invention has been described with reference to specific embodiments, modifications and variations of the invention may be constructed without departing from the scope of the invention.

TABLE I

Partial List of Chemical Targets

| Nucleic Acids | Oligos | Viruses | Acids |
|---|---|---|---|
| | c-DNA | Bacteria and it component parts such as epitopes, membranes, proteins, Etc. | Bases |
| | RNA | Cells (all kinds) | Chemicals affecting cell function and body function |
| | DNA | Membranes | Isoelectric Molecules (conditions) |
| | Other | Receptors | pH and pH influenced molecules |
| Antibodies | | Proteins | Ions |
| Enzymes | | Hormones | Toxins |
| BioDefense Agents | | Salts and Salt Concentrations | Buffering Agents |
| Pain Receptors | | Insecticides | Chemical Agents |
| Explosives | | Water Quality | Pb, Hg, and other |

TABLE I-continued

Partial List of Chemical Targets

| Nucleic Acids | Oligos | Viruses | Acids |
|---|---|---|---|
| | | Monitoring | hazardous metals |
| Prions | | Organic Chemicals | Inorganic Chemicals |
| Drugs | | Nerve Components | Organ Components |
| Signaling Chemicals | | Surface Chemicals | Symbiotic Chemicals |
| Buffering Solutions (component and concentrations) | | Gases | Liquids |
| Membranes | | IONS | Chemical Fractions |
| Other | | Insecticides | Aerosols |

TABLE II

A Partial List of Sensor Applications

| Drug sensitivity | Drug Efficacy | Medical Diagnostics | Cancer Diagnostics |
|---|---|---|---|
| Proteomics | Genetics | Toxic Analysis | Bio Defense |
| Plant Pathogen Sensing | Human Pathogen Sensing | Animal Pathogen Sensing | Bacteria Detection, Identification, Characterization and Measurement |
| Virus Detection, Identification, Characterization | Fundamental Biochemical Measurements | Binding Strengths of molecules (dissociation strengths and affinities) | "Receptor" properties |
| Chemical Thermodynamic Parameters | Chemical Reaction Dynamics | Multiple targets simultaneously | Biochemical Load |
| Cells | Cell chemicals | Cell Dynamics | Cell Division |
| Air Quality Monitoring | Food Quality Monitoring and Safety | Crop Diseases and Safety | Water Quality Monitoring and Safety |
| General Environmental Monitoring | Chemical Contamination | Chemical Constituents | Nutrition Monitoring and Diagnostics |
| Blood Banking | Public Heath Monitoring and Diagnostics | OSHA Chemical Monitoring | Laboratory Safety |
| Explosive Detection and Identification | Forensics | Chemical Properties (e.g., isoelectric point) | pH Measurement |
| Medical Technology | Materials Properties Including Thermodynamic Properties | Electronic Functions | Chemical Potential |
| Corrosion | Contact Potential | Threshold Voltage Considerations | Genotyping |
| Antibody typing | Drug Testing | Forensics | Chemical Accumulation and Collection |

The invention claimed is:

1. A sensing apparatus comprising a sensor comprising:
a substrate,
a sensing area in or on the substrate,
a protective region on the substrate located outside the sensing area and at least one selected from a group consisting of
a conductor region on the protective region outside the sensing area, and
a repellant blocking region on the sensor outside the sensing area, wherein the conductor region is not electrically connected to a sensor source or drain.

2. The apparatus of 1, wherein the conductor region is biased to protect the region surrounding the active sensor area from undesirable chemical attachment.

3. The apparatus of claim 1, wherein the conductor region comprises a surface protection bias.

4. The apparatus of claim 1, wherein the substrate comprises a sensor back gate bias.

5. The apparatus of claim 1, wherein the protective region comprises an insulator region around the conductor region.

6. The apparatus of claim 1, wherein the repellant blocking region comprises a biochemical repellant blocking region.

7. The apparatus of claim 1, wherein the repellant blocking region comprises an inert coating blocking region.

8. The apparatus of claim 1, wherein the repellant blocking region comprises a conductive shielding blocking region.

9. The apparatus of claim 1, further comprising a source coupled to the sensor.

10. The apparatus of claim 1, wherein the sensing area comprises a sensing region, a gate region on the sensing region, and an attachment region on the gate region for receiving and attaching material to be sensed.

11. The apparatus of claim 10, wherein the attachment region comprises receptors on the gate region for receiving and attaching targeted materials to only the sensing area.

12. The apparatus of claim 10, further comprising a light source, wherein the gate region is exposed to light from the light source for bonding pre-selected chemicals to the gate region.

13. The apparatus of claim 1, wherein the sensing area comprises a sensing region, at least one selected from a group consisting of an insulator, a conductor or a semiconductor on the sensing region, a gate region on the conductor, semiconductor or the insulator, and receptors on the gate region for receiving and attaching the targeted materials to only the sensing area.

14. The apparatus of claim 13, wherein the targeted materials comprise targeted biochemicals.

15. The apparatus of claim 14, wherein the receptors comprise a chemical attachment layer on the gate region for selective attachment of the targeted biochemicals.

16. The apparatus of claim 15, further comprising a light source for exposing the gate to light from the light source for binding of biochemicals where said biochemicals are at least one selected from a group consisting of
- receptor elements,
- targeted biochemicals, and
- blocking chemicals.

17. The apparatus of claim 1, wherein the repellant blocking region comprises a photo mask covering the protective region thereby isolating exposure of the materials to only the sensing area.

18. The apparatus of claim 17, wherein the photo mask is an opaque mask for masking the sensor except for the receptors to allow light from a light source to fall only on the sensing area.

19. A sensing apparatus comprising a sensor comprising:
- a substrate,
- a sensing area in or on the substrate,
- a protective region on the substrate located outside the sensing area and at least one selected from a group consisting of
- a conductor region on the protective region outside the sensing area, and
- a repellant blocking region on the sensor outside the sensing area, wherein the repellant blocking region is a chemical attachment region.

20. The apparatus of claim 19, wherein the protective region or the repellant blocking region is a biochemical region.

21. The apparatus of claim 19, wherein the protective region or the repellant blocking region is an inert coating region.

22. The apparatus of claim 19, wherein the protective region or the repellant blocking region is a conductive shielding region.

23. The apparatus of claim 19, wherein the repellant blocking region prevents sensor degradation by biochemical influences.

24. The apparatus of claim 19, further comprising a source coupled to the sensing area.

25. The apparatus of claim 19, further comprising a drain coupled to the sensing area.

26. The apparatus of claim 19, wherein the repellant blocking region comprises a photo mask covering the protective region thereby isolating ambient exposure to only the sensing area.

27. The apparatus of claim 26, wherein the photo mask is an opaque mask for masking the sensor except and selectively allowing light from a light source to fall only on the sensor's sensing area.

28. A sensing method using the apparatus of claim 19, the method comprising providing a sensor including:
- providing a substrate in the sensor,
- providing a sensing area in or on the substrate,
- attracting target material to be sensed,
- attaching the target material to the sensing area,
- providing a protective region on the substrate,
- isolating the sensing area from substrate areas outside the sensing area with the protective region,
- providing a repellant blocking region on the substrate outside the sensor surface,
- preventing the target material and other biochemicals from attaching to the other areas outside of the sensor surface with the repellant blocking region,
- enabling attachment of the target material to only the sensing area, and
- sensing the attached target material.

* * * * *